(12) United States Patent
Lyday

(10) Patent No.: US 6,524,587 B1
(45) Date of Patent: *Feb. 25, 2003

(54) HYPERTHERMIA AND IMMUNOTHERAPY FOR LEUKEMIAS LYMPHOMAS, AND SOLID TUMORS

(76) Inventor: Bruce W. Lyday, 12851 Haster St., #1-D, Garden Grove, CA (US) 92840

( * ) Notice: Subject to any disclaimer, the term of this patent is extended or adjusted under 35 U.S.C. 154(b) by 0 days.

This patent is subject to a terminal disclaimer.

(21) Appl. No.: 09/499,050

(22) Filed: Feb. 4, 2000

Related U.S. Application Data

(63) Continuation-in-part of application No. 09/073,322, filed on May 5, 1998, now Pat. No. 6,048,686.

(51) Int. Cl.$^7$ .......................... A61K 35/76; A61K 39/12; A61K 45/00

(52) U.S. Cl. ................................ 424/204.1; 424/278.1; 424/218.1; 424/93.6

(58) Field of Search ............................ 424/93.6, 204.1, 424/218.1, 278.1

(56) References Cited

U.S. PATENT DOCUMENTS 6,048,686 A * 4/2000 Lyday ............................ 435/5

OTHER PUBLICATIONS

Sinkovics and Horvath, "New Developments in the Virus Therapy of Cancer: A Historical Review", Intervirology, 1993, vol. 36, pp. 193–214.*

Islas–Rodriguez et al, "Efecto de la infeccion in vitro del virus del dengue (DEN–2) sobre algunas funciones de la respuesta immune celilar del raton", Archivos de Investigacion Medica (abstract), vol. 21, No.2, pp.87–93, 1990.*

Mettler et al, "Virus Inoculation in Mice Bearing Ehrlich Ascitic Tumors: Antigen Prouction and Tumor Regression", Infection and Immunity, vol. 37, No. 1, pp. 23–27, 1982.*

Angsubhakorn et al, "Neurovirulence detection of dengue virus using rhesus and cynomolgus monkeys", Journal of Virological Methods, vol. 18, No. 1, pp. 13–24, 1987.*

Eckels et al, "Isolation of a Temperature–Sensitive Dengue–2 Virus Under Conditions Suitable for Vaccine Development", Infection and Immunity, vol. 14, No. 5, pp. 1221–1227, 1976.*

Gabrilovitch et al, "Dendritic Cells in Antitumor Immune Responses", Cellular Immunology, vol. 170, No. 1, pp. 111–119, Jun. 1996.*

Mizoguchi et al, "Alterations in signal–transduction molecules in T–lymphocytes from tumor–bearing mice", Science, vol. 258, pp. 1795–1798, Dec. 1992.*

Kuss et al, "Clinical significance of decreased zeta chain expression in peripheral blood lymphocytes . . . ", Clinical Cancer Research, vol. 5, pp. 329–334, Feb. 1999.*

Gratama et al, "Restoration of expression of signal–transducing molecules in lymphocytes from patients with metastatic renal . . . ", Cancer Immunology, Immunotherapy, vol. 48, pp. 263–269, Aug. 1999.*

Kim et al, "Alteration of signal–transducing molecules and phenotypical characterization . . . ", Pathobiology, vol. 67, pp. 123–128, 1999.*

Chaturvedi et al, "Cytokine cascade in dengue hemorrhagic fever: implications for pathogenesis", FEMS Immunol Med Microbiol., vol. 28, pp. 183–188, Jul. 2000.*

Scott et al, "Dengue 2 vaccine: dose response in volunteers in relation to yellow fever status", J Infect Dis, vol. 148, pp. 1055–1060, Dec. 1983.*

Ben–Bassat et al, "Chemo–immunotherapy in patients with metastatic melanoma . . . ", Immunology Letters, vol. 33, pp. 127–134, Jul. 1992.*

G. Ada, "The coming age of tumor immunotherapy", Immunol Cell Biol, vol. 77, pp. 180–185, Apr. 1999.*

Hiraki et al, "Loss of HLA haplotype in lung cancer cell lines . . . ", Clin Cancer Research, vol. 5, pp. 933–936, Apr. 1999.*

Welt and Ritter, "Antibodies in the therapy of colon cancer", Semin Oncol, vol. 26, pp. 683–690, Dec. 1999.*

Becker et al, "Tumor escape mechanisms from immunosurveillance . . . ", Int Immunol, vol. 5, pp. 1501–1508, Dec. 1993.*

Paul et al, "HLA–G expression in melanoma . . . ", PNAS, vol. 95, pp. 4510–4515, Apr. 1998.*

*Dengue In The Caribbean, 1977*, No. 375, 1979, pp. 1, 8, 15, 16.

(List continued on next page.)

*Primary Examiner*—Anthony C. Caputa
*Assistant Examiner*—Karen A. Canella

(57) ABSTRACT

An improved method of inducing whole-body hyperthermia and enhanced anti-tumor immune response through inoculation of a fever virus with nil mortality and subsequent injection of irradiated tumor cells derived from the patient. This therapy will safely reduce the tumor burden by 90–99.9% by physical means (fever), before raising interferon levels to over 250 times baseline. The Activated Lymphokine Killer cells produced by these high interferon levels are capable of killing any cell expressing viral or tumor antigens, even those which had previously escaped immune surveillance. As a final step in the process, a specific class of Cytotoxic T Lymphocytes programmed to destroy the patient's own cancer cells will be produced by repeated inoculation of irradiated cancer cells harvested from the patient. Through a combination of three methods of therapy never previously integrated into a single regimen, it is logical to state that this therapy has a high probability of completely eradicating cancer cells from the patient. In addition, this therapy provides for life-long immunity to the reoccurrence of the disease.

30 Claims, No Drawings

OTHER PUBLICATIONS

Annika Håkansson et al, *On down–regulation of the immune response to metastatic malignant melanoma, Cancer Immunol Immunother*, vol. 48, 1999, pp. 253–262.

R.W. Schlesinger, *Dengue Viruses, Virology Monographs*, vol. 16, pp. 1–2, 48–50.

R. Walter Schlesinger, *The Togaviruses, Academic Press*, 1980, pp. 1, 107–117, 123–130, 132, 133, 146, 147, 157.

Ichiro Kurane et al., *Activation of T Lymphocytes in Dengue Virus Infections, J Clin. Invest.*, vol. 88, Nov. 1991, pp. 1473–1480.

Didier Hober et al., *Serum Levels of Tumor Necrosis Factor–α (TNF–α), Interleukin–6 (IL–6), And Interleuken–1β (IL–1β) in Dengue–Infected Patients, Am. J. Trop. Med. Hyg.*, vol. 83, No. 3, 1993, pp. 324–331.

Pontiggia P., Abstract for *Hypothermia in the treatment of brain metastases from lung cancer. Anticancer Res*, Mar.–Apr. 1995, vol. 15, No. 2, p. 1.

Amélia P.A. Travassos da Rosa et al., *Dengue Epidemic in Belém, Pará, Brazil, 1996–1997, Emerging Infectious Diseases*, vol. 63, No. 3, pp. 1–5.

Arie J. Zuckerman et al., *Principles and Practice of Clinical Virology, John Wiley & Sons, Ltd.*, pp. 1, 499, 500.

\* cited by examiner

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Target peptide for human CEA.

<400> SEQUENCE: 1

Tyr Leu Ser Gly Ala Asn Leu Asn Leu
 1               5

<210> SEQ ID NO 2
<211> LENGTH: 9
<212> TYPE: PRT
<213> ORGANISM: Artificial Sequence
<220> FEATURE:
<223> OTHER INFORMATION: Target peptide E75 for human HER-2/neu.

<400> SEQUENCE: 2

Lys Ile Phe Gly Ser Leu Ala Phe Leu
 1               5

HYPERTHERMIA AND IMMUNOTHERAPY FOR LEUKEMIAS LYMPHOMAS, AND SOLID TUMORS

This is a Continuation-in-part of U.S. patent application Ser. No. 09/073,322, filed May 5, 1998, now U.S. Pat. No. 6,048,686.

BACKGROUND

1. Field of Invention

This invention relates to hyperthermia and immunotherapy for treatment of cancer.

BACKGROUND

2. Description of Prior Art

The earliest references to treating cancer with hyperthermia can be found in Egyptian papyrus scrolls dated back to 3000 BC describing a breast cancer patient treated with immersion in hot water. Total body hyperthermia in the form of hyperpyrexia (fever) has produced dramatic tumor regressions and even cures following infection with pyrogenic bacteria. In the late $19^{th}$ and early $20^{th}$ centuries Dr. William Coley reviewed cases of spontaneous tumor regression and discovered that a common factor was a prolonged fever in excess of 39.5 degrees C. or 103.5 degrees F.

Dr. Coley tried to duplicate the fevers with *Streptococcus pyogenes* bacterial lysates, which contained the pyrogenic material lipopolysaccharide (LPS). Coley treated a wide variety of carcinomas and sarcomas with his Mixed Bacterial Toxins (MBT), achieving 5-year survival rates of 60% in inoperable malignant melanoma cases. These rates are considerably higher than those obtained using surgery, radiation, and chemotherapy programs. Problems developed when patients began producing large quantities of neutralizing antibody which required larger amounts of MBT. In addition, Coley had difficulty standardizing the pyrogenicity of the toxins. Coley remained convinced that a key portion of his treatment's success was based due to the enhanced immune response to the toxins, which somehow was cross-reactive against the tumors. Current knowledge of immunology confirms Coley's hypothesis, but it is now clear that antiviral immunity is much more closely related to antitumor immunity than the antibacterial response mechanisms.

This is due to the fact that bacterial infections primarily stimulate the humoral or antibody+complement arm of the immune system. For extracellular parasites such as bacteria and protozoa, this provides an efficient means of elimination within the bloodstream. Viruses, however, are intracellular parasites, and virus-infected host cells express viral antigens on their cell surface in conjunction with normal cell proteins. Hence, Killer Lymphocytes, with ability to recognize and kill virus-infected cells, are needed to eradicate the virus. Because cancerous cells also express "self" or normal host antigens on the cell surface along with "altered-self" or mutated tumor antigens, the same effector cells are needed. Natural Killer (NK), Lymphokine-Activated Killer (LAK), and antigen-specific Cytotoxic T Lymphocytes, have the primary responsibility of antitumor and antiviral surveillance and elimination. To date, there is no reference in the Scientific Literature to using a pyrogenic virus to induce whole-body hyperthermia.

Other techniques of inducing hyperthermia have been tried: immersion in hot liquids, limb perfusion, and even microwave radiation. The main disadvantage to these methods is that most cancers are deep within the tissue layers, and heating from the outside cannot generate a sufficient temperature to kill the tumor cells. Another problem with these prior-art approaches is that in metastasized cancer, tumor cells are spread throughout the body, and a treatment designed to be curative must heat the entire body as well. A whole-body pyremia approach utilizing a safe but pyrogenic virus solves these two difficulties.

Numerous versions of immunotherapy have been tried in cancer treatment, both specific and non-specific in nature. The primary non-specific immune modulator in cancer therapy has been Bacillus Calmette-Guerin, or BCG. BCG produces a Delayed-Type-Hypersensitivity (DTH) reaction which activates local macrophages to become tumorcidal in some cases. However, it is a poor pyrogenic agent, so hyperthermic benefits are not realized. Also, as detailed previously, it stimulates primarily the humoral arm of the immune system, so interferon production and NK activation are generally low.

Exogenous interferon therapies have been attempted, but suffer from purification and toxicity problems. Researchers have been able to achieve alpha-interferon levels 10 times higher than normal, but the response is hampered by Serum Blocking Factors (SBF) that neutralize the foreign interferon before it can induce a strong cellular response. Immunologists are in general agreement that therapies which stimulate endogenous interferon production are preferable to those which rely on injection of recombinant interferons and interleukins. The described immunotherapy stimulates endogenous interferon A levels approximately 260 times normal levels.

Numerous approaches to cancer vaccines have been attempted, with both sub-unit peptide and whole cell irradiated preparations generating a measurable response. In the case of malignant melanoma, polypeptide vaccines containing a common melanoma antigen: gp100, MART-1/Melan-A, and TRP-1, (Tyrosinase-Related Protein), have been clinically tested. The major drawback to these approaches is that being polypeptides, they can tolerize rather than induce a Killer Cell response. In addition, not all melanoma cells express these antigens in vivo to label them for identification and lysis by effector cells.

Another antigen-specific approach is to use whole cancer cells that have been killed in a manner (usually irradiation) that leaves their antigenic structure intact. These cells are then injected back into the body to induce an immune response. The problem with this approach is that the tumor burden must be reduced by physical means before the specific Cytotoxic T Lymphocytes are induced. The three major anticancer therapies: surgery, radiation, and chemotherapy reduce tumor burden but simultaneously devastate the immune system. The described therapy is designed to overcome these barriers.

Objects and Advantages

Accordingly, besides the objects and advantages of a whole-body, hyperthermic therapy based on pyrexia in response to a viral agent, several objects and advantages of the present invention are:

(a) to provide a means of reducing the tumor burden through a physical means (fever) in excess of 103.5 degrees F. which does not impair immune function.

(b) to induce billions of Natural Killer Lymphocytes to become Lymphokine-Activated Killers (LAK) cells capable of nonspecific tumorcidal activity.

(c) to induce a clone of Cytotoxic T Lymphocytes (CTL) capable of recognizing and destroying tumor cells bearing specific tumor antigens for the life of the patient.

(d) to accomplish the preceding activities without risk of serious harm to the patient.

Other objectives and advantages will become evident from the following detailed description of the invention and its operation.

DESCRIPTION OF INVENTION

Dengue virus is an RNA virus of the Togavirus Family, subfamily flavivirus. It has an icosahederal geometry, approximately 40–45 nanometers in diameter with two major envelope proteins. The E1 protein or Hemagglutin is very rich in the amino acid glycine, and has a molecular weight of approximately 45,000 daltons. The E2 protein or Neuraminidase is rich in the amino acids alanine, serine, and valine and has a molecular weight or approximately 50,000 daltons. The E3 protein is a transmembrane structure which anchors the E1 and E2 proteins to the viral core proteins. Neutralizing antibodies are primarily directed against the E1 protein.

MATERIALS AND METHODS

Patient Criteria.

Male or female subjects with stage I, II, III, or IV carcinomas, leukemias, or lymphomas.

Virus

Dengue Virus (available at Walter Reed Army Hospital, Washington, D.C.) passaged in African Green Monkey Kidney cells to less than 5 plaque-forming units /ml. DBS-FRhL-2 roller flasks are then inoculated with seed virus at a minimum of infection or MOI of 0.0005. After adsorption for 1.5 hrs. at 35 degrees Centigrade, the inoculum is removed and flasks are washed three times with 100 ml of Hanks balanced salt solution (HBSS). Maintenance medium (200 ml per roller) consisting of Eagle minimal essential medium with 0.25% human serum albumin, 0.22% NaHCO3, streptomycin (50 micrograms/ml), and neomycin (100 micrograms/ml). Medium on all flasks is changed by day four, and supernatant fluids harvested on day six. Before centrifugation at 1,050×g for 20 min., human serum albumin is to be added, resulting in a final concentration of 2.75%. Albumin pH is to be adjusted before addition to the viral fluids. As a final step in clarification, fluid is to be filtered through a 0.45 micrometer membrane filter (Nalge, Rochester, N.Y.) Samples are then to be tested for adventitious microbial agents to be performed as described in Public Health Service regulations for licensed, live-attenuated viral vaccines (Code of Federal Regulations, Chapter 21, subchapter F, Biologics).

After removal of samples for testing and plaque assay, remaining volume to be held in ice baths in a 4 degree C. refrigerator for 7 days pending results of safety testing and plaque assays. A final pool of virus to be made from fluids from flasks containing less than 5 plaque-forming units/ml at 39.3 degrees C., and no detectable large-plaque virus present. Average titer for vials to be 850,000 PFU/ml, then freeze-dried for use after neurovirulence testing. Intraspinal and intracerebral bihemispheric inoculation of 0.5 ml virus fluid of male rhesus monkeys with 2 controls receiving virus-free culture fluids. Monkeys to be observed daily for 20 days for evidence of CNS involvement or other physical abnormalities. Following sacrifice, histological examination of lumbar and cervical cord, lower and upper medulla oblongata, mesencephalon, and motor cortex to be made for viral pathology.

Preparation of Dendritic Cells

Bone Marrow cells are depleted for lymphoctytes and MHC Class positive cells by Fluorescent Activated Cell Sorting (FACS) with monoclonal antibodies for CD3, CD4, and CD8. Remaining cells are cultured overnight in Iscove's modified Dulbecco's medium (IMDM) supplemented with 10% Fetal Calf Serum (FCS), 2-ME, and 100 IU/ml penicillin, 1 mM sodium pyruvate, and 10 uM nonessential amino acids at 37 C in a 5% $CO_2$ atmosphere in 24-well plates with approximately 1 million cells in 1 ml culture medium/well. After 24 hours, the cells are replated and cultured in the presence of Granulocyte-Macrophage Colony Stimulation Factor (GM-CSF), and recombinant IL-4 at 900 U/ml. After 3 to 4 days, media to be exchanged for fresh cytokine media.

Alternatively, dermal dendritic cells (DDC) can be prepared using the following methods: Keratomes from healthy human volunteers are incubated in a solution of the bacterial proteases Dispase type 2 at a final concentration of 1.2 U/ml in RPMI 1640 for 1 hour at 37 C. After the incubation period, epidermis and dermis can be easily separated. Epidermal and dermal sheets are then cut into small (1–10 mm) pieces after several washing with PBS, and placed in RPMI 1640 supplemented with 10% Fetal Bovine Serum (FBS), and placed in 10-cm tissue culture plates. After 2–3 days, pieces of tissue are removed, and the medium collected. Cells migrating out of the tissue sections into the medium are spun down, resuspended in 1–2 ml fresh medium and stained with trypan blue. Further enrichment can be achieved by separation on a metrizamide gradient. Cells are layered onto 3-ml columns of hypertonic 14.5% metrizamide and sedimented at 650 g for 10 minutes at room temperature. Low density interphase cells are collected and washed in two successively less hypertonic washes (RPMI 1640 with 10% FBS and 40 mM NaCl ) to return cells to isotonicity.

Peptide Pulsing of Dendritic Cells

The previously described immunodominant peptides of the gene products can be constructed using a variety of methods, but one is described here. An Abimed 422 multiple peptide synthesizer at 10 micromole scale can be employed to construct the required peptides. Alternatively, genetic engineering techniques using cloning and expression vectors to yield milligram amounts of the desired peptides can be employed. After the desired peptides have been isolated in sufficient quantities, they must be loaded onto the DC. On day 8, DC can be pulsed for 2 hours at 37 C in 1 ml of IMDM supplemented with 0.5% BSA and 10 micrograms of peptide. After several isotonic washings, the peptides are ready for use in humans. The DC can be stored for up to two years at −50 C in liquid nitrogen stasis until ready for use.

Peptide Synthesis Procedure

Although many methods of synthesizing short chains of amino acids may be employed, the following method is described.

Step 1 (Synthesis)

Reagent grade methylene chloride to be distilled from anhydrous potassium carbonate Reagent grade dimethylformamide to be treated with 0.4 nm molecular sieves 48 hours prior to use. Additional materials and sources: (All materials are Reagent-Grade unless otherwise specified).

| Material | Commercial Source |
|---|---|
| Isopropanol | Fisher Chemical |
| Triflouroacetic acid | Eastman Chemical |
| Dicyclohexylcarbodiimide | Vega Biochemicals |
| Hydroxybenzotriazole | Sigma Chemical |
| Protected amino acids | Vega |
| Benzhdyrlamine resin 0.33 mmol/g | Pierce Biochemical |

Side chains of threonine and glutamic acid to be protected with O-benzyl groups, tyrosine by ortho-bromobenzyl-oxycarbonyl, and cysteine with S-para-methoxybenzyl. The inital amino acid (e.g., aspartic acid), converted to butoxycarbonyl-B-benzylaspartic acid, and coupled to the bezhydralamine resin. Coupling reactions to be checked at each step using ninhydrin and/or picric acid at the end of the cycle. Double-coupling will be necessary residues of aspartic acid, cysteine, proline, tyrosine, and phenylalanine. An equimolar amount of butoxycarbonyl-asparaginine to be included to prevent formation of cyanoalanine.

Following the final amino acid coupling, the N-terminal butoxycarbonyl group to be removed and the resin vacuum dried overnight to yield the peptide resin (95–97% pure). The peptide can be cleaved from the resin and the side-chain protective groups removed by the treatment of 1.0 g of resin plus 1.0 ml anisole with 20 ml liquid HF for 1.0 hour at 4 C. After removal of HF at 4 C with a stream of Nitrogen, the excess anisole can be removed by extraction with anhydrous ether (100) ml, with the resulting mixture to be exposed to high vacuum in the presence of NaOH pellets to remove any volatile HF. The crude peptide resin can be extracted with Nitrogen-deareated 5% HOAc (100 ml), to remove any remaining reagents. The resulting mixture to be diluted with water to 20% HOAc and put through a Sephadex G-10 column equilibrated with 20% HOAc. Final product to be lyophilized to yield final peptide

Injection of Patients

Patients to be injected by hypodermic needle into dermis with 2 ml of viral sample fluids once in each limb. After 2–3 days, patients to be infused by intralymphatic microcatheter with pulsed Dendritics, repeat injections until patient is negative for disease.

Operation of Invention a. Hyperthermia and Thermosensitivity of Cancer Cells

Cancer cells are more susceptible to heat than normal tissue cells due to many factors:

1. Tumor Type
2. Tumor Location
3. Blood Supply
4. Growth Rate
5. Intracellular pH
6. Cellular Metabolic Level Generally speaking, tumors arising from connective tissue (bone, cartilage, muscle) termed sarcomas are more susceptible to hyperthermia than tumors arising from lining or epithelial tissue called carcinomas. This is primarily due to the relative blood supplies of the tissue types. Epithelial tissue has a much richer blood supply than connective tissue, so carcinomas are more thermoresistant. Blood cancers such as leukemias and lymphomas are not susceptible to heat damage. Malignant melanomas share both characteristics as it arises from lining tissue, but has a poor blood supply.

The location is also critical, as limb tumors are easier to subject to selective heating than those in the body core. Most prior-art hyperthermic successes have been with limb perfusion of sarcomas. Tumors near an extensive network of arterioles are less sensitive than those far away from these main blood vessels.

The relative growth rate of the tumor is also critical. An aggressive, fast-growing tumor needs a richer blood supply than a dormant one. Fast-growing tumors also build up large pools of acidic metabolites, and this factor becomes critical during hyperthermia. At high temperatures, the spindle apparatus which stabilizes chromosomes during their replication is subject to denaturation and collapse, leading to cell death.

At moderate levels of hyperthermia (103.5–106 degrees F.), or (39.5–41 degrees C.) such as are induced by dengue fever, thermosensitivity is primarily due to indirect factors such as blood supply, intracellular pH, and cellular metabolism rates. Tumors have generally poor blood supply because they arise from a single cell, and soon outstrip the local blood supply. Secretion of a hormone called angiotensinogen encourages local blood vessel proliferation, but demand outpaces perfusion rates. In moderate to large tumors, the interior core is dead due to inability to obtain Oxygen, glucose, and other nutrients. Only the outer tumor cells are able to carry out sufficient gas and nutrient exchange for survival.

Tumors also have a lower intracellular pH than healthy tissue due to low perfusion to carry away toxic, acidic by-products of metabolism. Cells have two routes to generate the AdenosineTriPhosphate (ATP) currency molecules used to carry out functional reactions: Aerobic Metabolism and Glycolysis. Aerobic Metabolism uses oxygen and yields 36 ATP molecules per glucose molecule, with little acidic waste products. Glycolysis, on the other hand, is much faster, but yields only 2 ATP per glucose and produces lactic acid, which lowers intracellular pH.

Tumors have higher glycolysis rates than healthy cells because of their excessive growth. Thus, the tumor microenvironment is characterized by hypoxia (low Oxygen), acidosis, and nutrient deprivation. The stage is set for exploiting these weaknesses through hyperthermia.

When body temperature rises, so do cellular metabolism rates. Since enzymatic reactions generally increase as a function of temperature, cells must take in more nutrients and flush away their toxic wastes. Healthy cells, with normal perfusion rates, can easily stand temperatures of up to 41 degrees C. Tumor cells, on the other hand, are presented with a lose-lose scenario. If they do not increase their glycolytic rates, they will starve. If they do increase their glycolysis rate, their intracellular pH will fall until it reaches 6.7, almost a full logarithmic point below bloodstream pH. At 6.0, the enzymes responsible for critical cell reactions begin to fail, especially the Na-K ATPase pump system. This enzyme is responsible for maintaining the relative gradient of sodium and potassium ions across the cell membrane. When it fails, sodium ions flood in, and the cell dies. Lysosomes and peroxisomes are cytoplasmic membrane-bound bodies containing proteases. At pH of 6.0 and below, these bodies rupture, digesting the cell.

Tumor sensitivity is both time and temperature-dependent, according to the reaction: $s=Soe^{-kt}$ where s is survival at any given time t and So is survival at initial time and k is a constant representing inactivation rate at given temperature and t is the duration of incubation.

As can be seen from the above equation, cell survival decreases logarithmically. In simple terms, the higher the temperature, the shorter the time period needed for a 1 log or 90% tumor kill rate, a 2 log or 99% kill rate, or a 3 log, or 99.9% kill rate.

Dengue fever produces temperatures sufficient to produce a 1–2 log reduction in viable tumor cells, but a comparatively small number will survive if they are located near high-perfusion vessels. It is now up to the immune response to identify and eliminate the cells.

b. Active non-specific immunotherapy operation of invention Dengue fever virus infects and reproduces in two kinds of white blood cells: immature monocytes (which mature into macrophages), and B-Lymphocytes, which mature into antibody-producing Plasma Cells. In the first three days on infection, dengue kills 60% of the circulating white blood cells, dropping WBC counts from 5300/ml to 2200/ml. When ruptured, these cells liberate massive amounts of interferon, interleukins, and lymphocyte structural proteins into the bloodstream. These lymphokines stimulate NK cells to become LAK cells, which are capable to killing viral-and tumor-antigen expressing cells without regard to specificity. In previous in vitro experiments, dengue-activated LAK cells killed cells of the human tumor line K562 to a high degree. LAK cells are capable of killing tumor cells that are resistant to NK cells, and this is a critical factor in the operation of the invention.

Dengue also induces mature macrophages to become tumorcidal through a lymphokine called MAF or Macrophage Activation Factor. In this state, macrophages become Tumor-Infiltrating Leukocytes capable of killing cancerous cells. Even though this response, following a 1–2 log kill through hyperthermia, may very well eradicate tumor cells from a patient, yielding a cure, it will eventually subside. To be completely certain that no cancer cell survives the heat and the LAK/TIL response, a third component, one that provides for lifelong anti-tumor surveillance and killing capability, is required.

c. Specific Anti-tumor Response of Invention

LAK cells, while possessing formidable tumorcidal properties, have no immunological memory. After interferon levels return to normal, these nonspecific killer cells have no capacity for "remembering" the antigenic structure that triggered them to destroy a cell. That function of the immune system is delegated to the antibody arm of the humoral immunity, and to the Cytotoxic T Lymphocytes.

Cytotoxic T Lymphocytes are derived from the Thymus, and migrate to lymph tissue. Although T4 Helper lymphocytes can be cytotoxic to tumor cells, these recognize longer peptides presented by Class II MHC on a limited number of cell types. T8 CTL recognize shorter (8–11 mer) peptides presented by Class I MHC, present on all cell types except in "privileged" sites: CNS, retina, and gonads. T8 CTL use their T-Cell Receptor (TCR), to evaluate peptides presented by MHC proteins coded for by the HLA A and B alleles. Proteins manufactured in the endoplasmic reticulum are periodically cut by proteases, and peptides fitting the HLA binding motif are loaded between the MHC chains. Thus stabilized, the trimeric complex eventually is embedded in the cell membrane, where the peptide can be "read" by the TCR. Cells producing viral proteins, or tumor-related peptides, can thus be eliminated if sufficient numbers of CTL can be generated. These CTL are memory-competent, and can identify and kill cells expressing their target antigens for the lifetime of the patient.

Many cancer researchers have attempted to generate tumor-specific CTL with limited success. The major difficulties arise from a lack of prior debulking, the seven tumor immune evasion methods, and T-cell tolerance to self-peptides.

Tumor Debulking

Elimination of 99% (2-logs) of the existing tumor cells is a requirement for optimum results from immunotherapy. Chemotherapy using cytotoxic drugs, gamma-radiation, and major surgery can debulk the tumor, but depress cellular immunity. Patients sometimes are "cured" of their cancer by these methods only to die from infection due to their depressed immune system. Hyperthemia is the only reliable debulking method which does not suppress cellular immune responses.

The Seven Tumor Immune Evasion Methods

If a therapy achieves 2-log debulking, CTL and LAK cells are often unsuccessful in eliminating tumor cells due to the seven tumor immune evasion methods.
1. Down-Regulation of Class I MHC expression.
2. Point Mutations in tumor epitopes recognized by CTL.
3. Expression of fetal trophoblast HLA-G protein to avoid NK recognition.
4. Tumor microvessels are inhibitory to LAK and CTL migration.
5. Tumor cells induce monocytes to secrete IL-10, which renders CTL anergic.
6. Tumor cells express Fas Ligand (FasL), which can kill Fas+CTL.
7. Tumor cells erect fibrous stromal barriers to impede CTL movement.

The described invention is engineered to defeat all seven of these mechanisms through the release of cytokines induced by the dengue virus.

Tumor cells often decrease or eliminate Class I MHC expression by restricting the beta-2-microglobin, which forms the floor of the MHC trimer. Without B-2m, the MHC is unstable and cannot bind peptide. Tumor cells also decrease the transporter proteins TAP-1 and TAP-2, which carry the MHC complex to the membrane. Dysfunction of these proteins leads to absent Class I expression, rendering the tumor cell invisible to the T-Cell Receptor of the CTL.

Dengue virus infection induces large amounts of interferons alpha, beta, and gamma. IFN-gamma can restore Class I expression in tumor cells by binding to the promoter regions of the B-2m and TAP genes. IFN-alpha also increases Class I expression, and acts in synergy with IFN-gamma to elevate Class I levels to normal.

Tumor cells often suffer from high mutation rates as a result of faulty gene regulation, and mutations in target peptides recognized by tumor-specific CTL can help the tumor cell avoid lysis. If the mutation occurs in an amino acid required for anchoring the peptide to the MHC chain, that peptide can no longer bind an HLA molecule. If the mutation occurs in a residue required for TCR recognition, the peptide will still bind MHC, but will no longer be recognized by the CTL.

Dengue infection results in high levels of two important cytokines: IFN-beta, and IL-2. When CTL are exposed to these cytokines together, they lose target specificity and acquire LAK-like lytic ability. These non-fastidious CTL can lyse tumor types from many cell lines without HLA-restriction, so mutations in tumor-related peptides should not allow escape.

Tumor cells that have decreased MHC expression are vulnerable to NK lysis. Natural Killers use a receptor that transmits a negative signal when bridged by Class I MHC. If the cell lowers its HLA expression, it can be killed by NK cells. Fetal trophoblast cells express a protein termed HLA-G, which protects from maternal NK lysis. Tumor cells that activate the HLA-G gene while decreasing their Class I MHC levels can avoid both arms of the cellular immune system Dengue infection induces very high levels of IL-2, which drives CTL proliferation. IL-2 also transforms NK cells into LAK, which can kill NK-resistant tumor lines like the Renal Cell Carcinoma line Cur.

Tumor blood vessels, especially the High Endothelial Venules (HEV), often lack the P and E selecting, which ligate the CD11 integrins found on activated killer cells. Together with high hydrodynamic shear rates, this prevents LAK and CTL from exiting the bloodstream to engage the tumor cell targets.

Dengue infection induces high levels of two proinflammatory cytokines, IL-1 and Tumro Necrosis Factor-alpha (TNF-a). IL-1 and TNF-a up-regulate the selectins on tumor vessels, and widen the gap junctions between vessel endothelial cells. This allows the killer cells created by the therapy to exit the HEV and destroy tumor cells.

Tumor cells often secrete Transforming Growth Factor-Beta (TGF-b), which causes monocytes in the vicinity to secrete IL10. IL-10 renders CTL anergic, so that they are no longer capable of engaging tumor cells. Dengue virus selectively reproduces in and kills monocytes, and the high levels of IL-2 induced will reverse the anergic state of the tumor-infiltrating lymphocytes (TIL).

CTL cloned in response to a pathogen often express Fas, or CD95. When bridged by the Fas ligand (FasL), the CTL dies by DNA fragmentation (apoptosis). Cells in "privileged" sites often express FasL to kill any CTL intruding into sensitive areas. Tumor cells that express FasL can kill responding CTL, allowing for unchecked tumor growth.

Dengue infection induces high amounts of IL-6, which promotes expression of FLIP (Fas-Ligand inhibitory Protein). FLIP acts as a "safety switch" covering the Fas self-destruct trigger on CTL. As long as IL-2 levels are high, FLIP will protect CTL from FasL. IL-2 levels in dengue infection stay high for over 30 days.

Tumor cells secrete factors promoting growth of fibrovascular bundles called stroma. This dense network of collagen bundles can impede CTL mobility. The high levels of IFN-gamma induced by dengue infection activate macrophages to express CD44, which digest stromal barriers with hyaluronidase enzymes. The activated macrophages will be drawn to tumor areas by chemotactic signals released by tumor-specific T4 and T8 CTL.

Overcoming T-cell Tolerance to Tumor-Related Peptides

The therapy described herein is unique due to its design to defeat each tumor immune evasion method. A therapy achieving the first two goals, debulking and defeating the tumor immune evasion mechanisms, has one other barrier to overcome: T-cell Tolerance.

In the last months in utero, and for the first 18 months of life, the T-cell immune system undergoes a cycle of clonal selection and deletion. T4 and T8 cells with receptors that have a high affinity for self-peptides presented by the thymic epithelium are eliminated (deletion). Only T-cells with low affinity for self-peptides are selected for, and leave the Thymus to reside in peripheral lymph tissue. This is an important safeguard against autoimmunity, but tumor cells take advantage of this system. If the tumor arouses an immune response, the CTL created will have low affinity for the peptide, and so exhibit low cytotoxicity against the tumor cells. Combined with the immune evasion methods, this explains the low rates of success in tumor immunotherapies.

Clonal deletion is a less than perfect process, or autoimmune diseases would be unknown. There is a growing body of evidence suggesting that tolerance can be overcome, given the proper conditions. The first requirement is for efficient presentation of antigen to the T-cells. Macrophages can function as antigen-presenting cells (APC), but the most efficient APC are Dendritic Cells (DC), derived from bone marrow. DC capture antigen, process it into target peptides, then present the peptide to T-cells. The CTL then mold their TCR to recognize the peptide, and become antigen-specific.

DC can prime CTL at rates of 1:1000, so 10 million DC pulsed with tumor peptides can generate 10 billion CTL. Following a 2-log reduction through hyperthermia from an initial tumor burden of 10 billion cells, this will result in 100 CTL to each remaining tumor cell.

The second requirement for overcoming T-cell tolerance is high levels of Th1-type cytokines: IFN-gamma, IL-2, IL-7, and IL-12. CTL expansion is limited by two factors: APC and Th1 cytokine levels. Dengue infection induces the high levels required.

Tumor-Associated Antigens (TAA)

Another major drawback to successful tumor immunotherapy is the scarcity of TAA to serve as targets for CTL. Unlike the peptides captured by HLA in virus-infected cells, TAA are generally synthesized in lower amounts. Each cell has approximately 200,000 copies of a specific HLA type, HLA-A2, for example. Each peptide fragment must compete with 10,000 others for HLA-binding, and a minimum of 200 MHC complexes presenting the peptide are required for CTL lysis.

Melanoma has the best-characterized TAA: Melan-A/MART-1, gp100, pmel7, and the MAGE group antigens, which are expressed on other tumor types. The following tumor types are listed, with specific TAA that can be loaded onto allogenic DC to prime tumor-specific CTL:

Adenocarcinoma of the Breast

The most frequently expressed TAA by breast cancers are CarcinoEmbryonic Antigen (CEA), and HER-2/neu, a proto-oncogene. CEA is a large fetal oncoprotein expressed in large amounts in various adenocarcinomas, but in only minor amounts in ordinary small intestinal epithelium tissue. An example of a target peptide is YLSGANLNL (SEQ ID NO:1), restricted by HLA-A2. HER-2/neu is overexpressed in many tumor types, and is a large (1255 amino acids) protein with many suitable targets for CTL. An example of a target peptide is E75, containing residues 369–377, KIFGSLAFL (SEQ ID NO:2). HER-2/neu is expressed up to 200-fold in tumor cells from breast, ovarian, and lung tissue.

Cervical Cancer

Cervical cancers are associated with the Human Pappiloma Virus (HPV) types 17 and 19. These DNA viruses are genetically stable, unlike the RNA viruses Influenza A and HIV-1. HLA-restricted HPV peptides have been identified as targets for CTL.

Colon Cancer

Colon cancer shares similar targets with breast cancer: CEA and HER-2-neu.

Gastric Cancer

Stomach cancer cells have been found to over-express HER-2/neu.

Head and Neck Cancer

Head and Neck Squamous Epithelial cancers have been found to over-express the melanoma-associated peptides from the MAGE-1 and MAGE-3 genes.

Leukemias and Lymphomas

Although unaffected by hyperthermia, as they are floating in an oxygen-rich medium, leukemic and lymphoma cells are vulnerable to LAK cells. They also express peptides from the oncogenes N-ras and K-ras, associated with Chronic Myelogenous Leukemia and Acute Myeloid Leukemia. T-cell leukemias are frequently caused by the Human T-Lymphotropic Leukemia viruses HTLV-1 and II. The viral peptides presented by HLA in leukemic cells can serve as targets for CTL.

The Epstein-Barr Virus is a large DNA virus associated with nasopharyngeal carcinoma and Non-Hodgkin's Lymphoma. The peptides from this virus are expressed by the cancer cells and can serve as targets for CTL.

Lung Cancer

Lung cancers are divided into squamous and adenocarcinomas. Target peptides restricted by Aw68 have been isolated from squamous lung cancers, and adenocarcinomas share peptides from the HER-2/neu, MAGE, GAGE, and related BAGE genes.

Prostate Cancer

Prostate-Specific Antigen has been used as a diagnostic marker for prostate cancer, but it also contains CTL epitopes. Examples restricted by HLA-A2 are PSA-1, and PSA-3.

Ovarian Cancer

Ovarian cancer cells have been found to express HER-2/neu and CEA.

Pancreatic Cancer

Pancreas cancer cells have been found to express HER-2/neu and CEA.

Renal Cell Carcinoma

Renal Cell Carcinomas share many melanoma-related peptides, including MAGE and GAGE.

Uterine Cancer

Uterine cancer cells have been found to express HER-2/neu and CEA.

Tumor-Related Peptides Expressed as Part of the Carcinogenesis Process p53 Tumor Suppressor Protein The product of the p53 gene is a cornerstone of the carcinogenesis process. Its product is a tetrameric protein that binds to DNA. This acts as a barrier to RNA Polymerase II binding, preventing transcription of an oncogene. Mutations arising from UV radiation, chemical carcinogens, infection with a tumor-causing virus like SV40 can inactivate p53. Inactivated p53 can no longer prevent transcription, and the oncogene becomes activated, transforming the cell into an immortal, rapidly proliferating tumor cell.

Mutated p53 genes are found in over 50% of all cancers, and peptides from these genes are HLA-restricted. CTL specific for mutated p53, or even for tumor cells over-expressing normal p53, can eradicate tumors in mice. For this type of peptide to be used in cancer patients, the Class I MHC types can be compared to cDNA libraries of p53, then the Polymerase Chain Reaction (PCR), can be used to confirm the presence of mutated p53 in tumor tissue samples.

Telomerase

The second general TAA is the enzyme telomerase. The ends of chromosomes are capped by repeating units of telomeric DNA. This prevents unraveling of the chromosome, as well as interchromosomal binding. Telomeric DNA is lost each time a cell divides, and due to the semi-conservative nature of DNA replication, they cannot be replaced by DNA Polymerase I. This appears to serve as a cellular clock, limiting the number of times a cell can divide. When the telomeres reach termination, the cell goes into arrest, unable to divide further.

Cancer cells, by definition, proliferate rapidly in defiance of restraints against such activity. To add telomeres, they must synthesize large amounts of the enzyme telomerase. Close to 90% of tumor cell lines show high telomerase expression, and the catatlytic sub-unit, (hTERT) is an HLA-restricted protein capable of serving as a target for CTL. Since telomerase is not usually synthesized by normal cells, it represents a widely-expressed TAA for immunotherapy.

Although most TAA are present in some normal tissue types, especially rapidly proliferating ones, they are made in minute amounts. Because the TAA have to compete with 10,000 peptides derived from normal proteins, the HLA presentation of these is low.

Conclusion, Ramifications, and Scope

Accordingly, the reader will see that the combined therapy previously described provides a safe and effective means for eliminating cancer cells from a human body. By combining three methods known to medicine as beneficial to cancer patients, the therapy solves the dilemma posed by current chemotherapy, radiation, and surgery. The above and various other objects and advantages of the present invention are achieved without undue risk to the patient, as full-strength wild-type dengue virus has a mortality rate given by various Tropical Medicine texts as nil, nonexistent, and 1 in 61,000. No other reference to injecting volunteers with any other full-strength virus could be found in any journal.

Although the description above contains many specifics, these should not be construed as limiting the scope of the invention but as merely providing illustrations of some of the presently preferred embodiments of this invention.

Thus the scope of this invention should be determined by the appended claims and their legal equivalents, rather than by the examples given.

Unless defined otherwise, all technical and scientific terms used herein have the same meaning as commonly understood by one of ordinary skill in the art to which this invention belongs. Although any materials and methods similar or equivalent to those described herein can be used in the practice or in vitro and in vivo testing of the present invention, the preferred methods and materials are described. All publications mentioned hereunder are incorporated herein by reference. Unless mentioned otherwise, the techniques employed herein are standard methodologies well known to one of ordinary skill in the art.

The term "substantially pure" as used herein means as pure as can be obtained by standard purification techniques.

I claim:

1. A method of reducing tumor burden in a cancer patient with a human solid tumor, comprising the steps of:
   injecting said patient with substantially pure Dengue Virus; and
   maintaining body temperature of said patient in excess of 103.5 degrees F. for a sufficient period of time to reduce tumor burden, wherein said Dengue virus injection maintains said body temperature in excess of 103.5 degrees.

2. The method of claim 1 wherein said virus is selected from the group consisting of Dengue Type 1, Type 2, Type 3, and Type 4 Serotypes of the Family Togaviridae.

3. The method of claim 1 wherein said substantially pure Dengue Virus has been tested to confirm the elimination of neurovirulence by passing said virus through subhuman primates.

4. The method of claim 1 wherein the purification of said substantially pure Dengue virus begins with passage of said virus through cells with an active transmembrane gradient.

5. The method of claim 4 wherein said cells are infected with virus at less than 5 $\log_{10}$ plaque-forming units/ml.

6. The method of claim 1 further comprising injecting said patient with allogenic Dendritic cells pulsed with tumor peptides; and repeating the injection of said Dendritic Cells in said patient until cancer cells in said patient are reduced.

7. The method of claim 4 wherein said cells with an active transmembrane gradient are Green Monkey Kidney cells.

8. A method of reducing tumor burden in a cancer patient with leukemia or lymphoma comprising the steps of;
   injecting said patient with substantially pure Dengue Virus; and
   maintaining body temperature of said patient in excess of 103.5 degrees F. for a sufficient period of time to reduce tumor burden, wherein said Dengue virus injection maintains said body temperature in excess of 103.5 degrees F.

9. The method of claim 8 wherein the purification of said substantially pure Dengue virus begins with passage of said virus through cells with an active transmembrane gradient.

10. The method of claim 8 wherein said cells are infected with virus at less than 5 $\log_{10}$ plaque-forming units/ml.

11. The method of claim 8 further comprising injecting said patient with allogenic Dendritic cells pulsed with tumor peptides; and repeating the injection of said Dendritic Cells in said patient until cancer cells in said patient are reduced.

12. The method of claim 6 wherein said cancer cells are melanoma cells and said tumor peptide is selected from the group consisting of: Melan-A/MART-1, gp100, pme17, and the MAGE group antigens.

13. The method of claim 6 wherein said cancer cells are adenocarcinoma cells of the breast and said tumor peptide is CarcinoEmbryonic Antigen (CEA) or HER-2/neu.

14. The method of claim 6 wherein said cancer cells are Cervical cancer cells and said tumor peptide is selected from the group consisting of any proteins from Human Papiloma Virus type 17 or 19.

15. The method of claim 6 wherein said cancer cells are Colon cancer cells and said tumor peptide is CarcinoEmbryonic Antigen (CEA) or HER-2/neu.

16. The method of claim 6 wherein said cancer cells are gastric cancer cells and said tumor peptide is HER-2/neu.

17. The method of claim 6 wherein said cancer cells are head and neck cancer cells and said tumor peptide is the MAGE-1 or MAGE-3 proteins.

18. The method of claim 6 wherein said cancer cells are lung cancer cells and said tumor peptide is selected from the group consisting of: Aw68, HER-2/neu, MAGE, GAGE, and BAGE proteins.

19. The method of claim 6 wherein said cancer cells are prostate cancer cells and said tumor peptide is selected from the group consisting of: HLA-A2, PSA-1, and PSA-3.

20. The method of claim 6 wherein said cancer cells are Ovarian cancer cells and said tumor peptide is CarcinoEmbryonic Antigen (CEA) or HER-2/neu.

21. The method of claim 6 wherein said cancer cells are Pancreatic cancer cells and said tumor peptide is Carcino-Embryonic Antigen (CEA) or HER-2/neu.

22. The method of claim 6 wherein said cancer cells are Renal cell carcinoma cells and said tumor peptide is MAGE and GAGE proteins.

23. The method of claim 6 wherein said cancer cells are Uterine cancer cells and said tumor peptide is CarcinoEmbryonic Antigen (CEA) or HER-2/neu.

24. The method of claim 6 wherein said tumor peptide is p53 or telomerase.

25. The method of claim 24 wherein said cancer cells are nasopharyngeal carcinoma cells and said tumor peptide is a peptide from EBV.

26. The method of claim 11 wherein said tumor peptide is p53 or telomerase.

27. The method of claim 11 wherein said cancer cells are Leukemia and Lymphoma cells and said tumor peptide is selected form the group consisting of: N-ras, K-ras, HTLV-1 proteins, HTLV-2 proteins, and EBV viral proteins.

28. The method of claim 27 wherein said Leukemia cells are Chronic Myelogenous Leukemia and Acute Myeloid Leukemia cells and said tumor peptide is N-ras or K-ras.

29. The method of claim 27 wherein said Leukemia cells are T-cell Leukemia cells and said tumor peptide is a peptide from HTLV-I or HTLV-II.

30. The method of claim 27 wherein said lymphoma cells are non-Hodgkins lymphoma cells and said tumor peptide is a peptide from EBV.

* * * * *